(12) United States Patent
Hyacinthe (10) Patent No.: US 7,722,838 B2
(45) Date of Patent: May 25, 2010

(54) SYSTEM AND DEVICE FOR PREVENTION AND NEUTRALIZATION OF BIOACTIVE SUBSTANCES AND GENERATING AN AROMA-PRODUCING SUBSTANCE

(75) Inventor: Berg P. Hyacinthe, Tallahassee, FL (US)

(73) Assignee: GRAHN - Monde Groupe de Reflexion & D'Action, Montréal, Quebec (CA)

( * ) Notice: Subject to any disclaimer, the term of this patent is extended or adjusted under 35 U.S.C. 154(b) by 1170 days.

(21) Appl. No.: 11/330,875

(22) Filed: Jan. 12, 2006

(65) Prior Publication Data

US 2007/0020153 A1    Jan. 25, 2007

Related U.S. Application Data

(60) Provisional application No. 60/700,708, filed on Jul. 19, 2005.

(51) Int. Cl.
| | |
|---|---|
| A61L 9/00 | (2006.01) |
| A61L 2/00 | (2006.01) |
| A62B 7/08 | (2006.01) |
| G05D 7/00 | (2006.01) |
| A24F 25/00 | (2006.01) |
| A01G 27/00 | (2006.01) |
| B05B 1/28 | (2006.01) |
| A61M 11/06 | (2006.01) |
| A61K 38/46 | (2006.01) |

(52) U.S. Cl. ............... 422/305; 422/1; 422/5; 422/20; 422/28; 422/119; 422/120; 422/110; 422/116; 422/123; 422/124; 422/306; 239/57; 239/69; 239/102; 239/301; 239/303; 239/320; 239/338; 424/94; 424/94.6

(58) Field of Classification Search ............... 422/1, 422/5, 20, 28, 119–120, 110, 116, 123–124, 422/305–306; 239/57, 69, 102, 301, 303, 239/320, 338; 424/94, 94.6
See application file for complete search history.

(56) References Cited

U.S. PATENT DOCUMENTS

| | | | | |
|---|---|---|---|---|
| 5,591,409 | A * | 1/1997 | Watkins | 422/110 |
| 5,592,940 | A * | 1/1997 | Kampfe et al. | 600/431 |
| 5,972,290 | A * | 10/1999 | De Sousa | 422/5 |
| 6,631,888 | B1 * | 10/2003 | Prueter | 261/30 |
| 2002/0048610 | A1 * | 4/2002 | Cima et al. | 424/725 |
| 2002/0127623 | A1 * | 9/2002 | Minshull et al. | 435/7.92 |
| 2003/0192959 | A1 * | 10/2003 | Hess et al. | 239/69 |

* cited by examiner

*Primary Examiner*—Jill Warden
*Assistant Examiner*—Monzer R Chorbaji (57) ABSTRACT

An on-demand system for preventing and/neutralizing bioactive substances employs real time monitoring of the fluid for bioactive substances. Once a specific bioactive substance is detected, then a specific neutralizing substance is selected, such as an oxidizing substance, intense ultraviolet light, a neutralizing substance or other substances selected for particular threats. In another example of the invention, a device neutralizing a substance would include a container that would be capable of containing each of the plurality of precursors, a collecting space for receiving each of the plurality of precursors selected by the selector, and a dispensing mechanism for dispensing the neutralizing substance. In one example the neutralizing substance is formulated by the reactions of the precursors in order to neutralize the substance. The device may alternatively select a plurality of precursors to produce an aroma-producing substance and alternatively may neutralize the aroma-producing substance if it harmful or lethal, for example.

39 Claims, 9 Drawing Sheets

Figure 5:
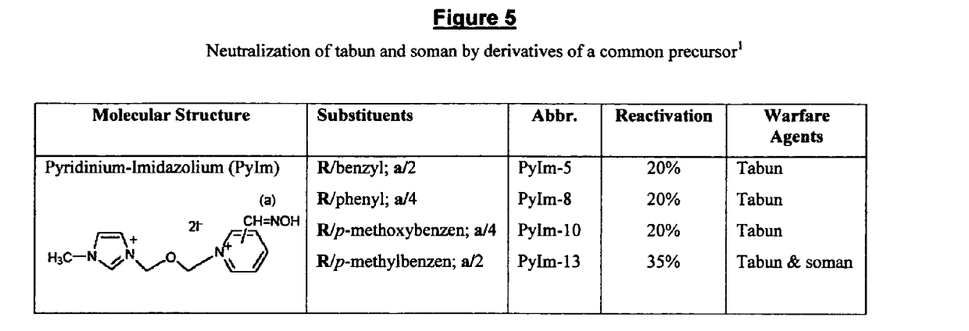

Figure 5
Neutralization of tabun and soman by derivatives of a common precursor[1]

| Molecular Structure | Substituents | Abbr. | Reactivation | Warfare Agents |
|---|---|---|---|---|
| Pyridinium-Imidazolium (PyIm) (a) | R/benzyl; a/2 | PyIm-5 | 20% | Tabun |
| | R/phenyl; a/4 | PyIm-8 | 20% | Tabun |
| | R/p-methoxybenzen; a/4 | PyIm-10 | 20% | Tabun |
| | R/p-methylbenzen; a/2 | PyIm-13 | 35% | Tabun & soman |

Figure 6:
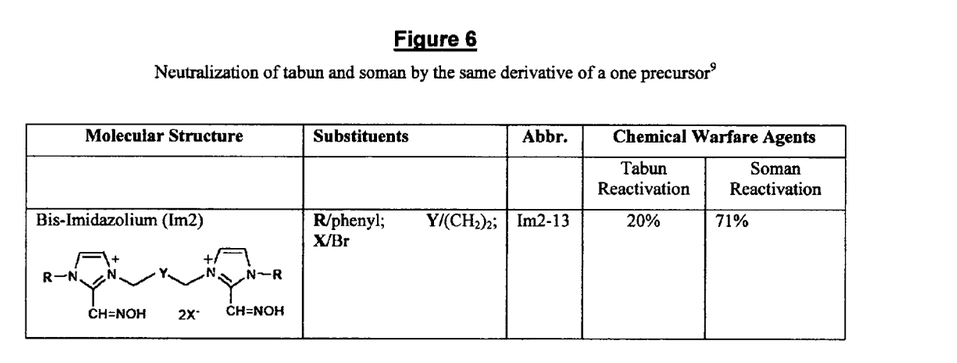

Figure 6
Neutralization of tabun and soman by the same derivative of a one precursor[9]

| Molecular Structure | Substituents | Abbr. | Chemical Warfare Agents | |
|---|---|---|---|---|
| | | | Tabun Reactivation | Soman Reactivation |
| Bis-Imidazolium (Im2) | R/phenyl; Y/(CH$_2$)$_2$; X/Br | Im2-13 | 20% | 71% |

Figure 7

Figure 8

Airborne Poisonous Gas

Scattered Beams

Microscopic Objective

Capturing Beams

Figure 9

Figure 10

Neutralization of sarin and VX by derivatives of a common precursor[9]

| Molecular Structure | Substituents | Abbr. | Chemical Warfare Agents | |
|---|---|---|---|---|
| Bis-Pyridinium (Py2) (a) HON=HC–[pyridinium]–N⁺–O–N⁺–[pyridinium]–R (b), 2I⁻ | R/ [pyridine] a/2; b,/4 | Py2-62 | Sarin | VX |
| Bis-Pyridinium (Py2) (HON=HC–[pyridinium]–N⁺–O–N⁺–[pyridinium])₂, 4I⁻ | a/2 | Py2-66 | Sarin | VX |
| | a/4 | Py2-67 | Sarin | VX |
| | | Py2-68 | Sarin | VX |

SYSTEM AND DEVICE FOR PREVENTION AND NEUTRALIZATION OF BIOACTIVE SUBSTANCES AND GENERATING AN AROMA-PRODUCING SUBSTANCE

CROSS-REFERENCE TO RELATED APPLICATION

The present application claims the benefit of previously filed co-pending Provisional Patent Application, Ser. No. 60/700,708 filed Jul. 19, 2005.

FIELD OF THE INVENTION

The field relates to degustation and olfaction, sensors for artificial degustation and olfaction, automatic identification of bioactive substances and neutralization of such substances.

BACKGROUND OF THE INVENTION

It is known to use filters to actively or passively remove bioactive substances from air and water. However, such filters must always be present, even if no bioactive substances are present that are intended to be filtered or neutralized. These filters must be replaced periodically, or the filter efficiency reduces as the filter becomes clogged, and the ability of the filters to neutralize bioactive substances decreases as any active substances degrade. In many respects, human-computer interaction (HCI) researchers analyze and design specific user interface technologies with the ultimate goal to meet a particular information need through all five senses. However, only three (sight hearing, and touch) of these senses have been fully exploited. The unexploited senses of smell and taste raise cyber-security implications. Cybernetics is considered as the replication or imitation of biological control systems with the use of technology. The term itself originated in 1947 when Norbert Wiener used it to name a discipline apart from, but touching upon, such established disciplines as electrical engineering, mathematics, biology, neurophysiology, anthropology, and psychology (Wiener, 1948).

Improved systems and devices integrating new advances in technology are currently being developed and often require interdisciplinary approaches. The apparatus described in this disclosure uses such an interdisciplinary approach.

SUMMARY OF THE INVENTION

An on-demand system for preventing and/neutralizing bioactive substances employs real time monitoring of the fluid for bioactive substances. Once a specific bioactive substance is detected, then a specific neutralizing substance is produced or generated, such as an oxidizing substance, intense ultraviolet light, a neutralizing substance or other substances selected for particular threats. The selected substances dispersed in a fluid stream or within a filter medium in order to neutralize or inactivate the bioactive substance.

The device for neutralizing a substance would include a container that would be capable of containing each of the plurality of precursors, a collecting space for receiving each of the plurality of precursors selected by the selector, and a dispensing mechanism for dispensing the neutralizing substance. In one example, the neutralizing substance is formulated by the reactions of the precursors in order to neutralize the substance.

The system includes a detecting system capable of detecting and identifying a plurality of substances to be neutralized; an analysis system capable of selecting a neutralizing substance capable of neutralizing the substance to be neutralized, a selection system capable of selecting a plurality of precursors needed to form the neutralizing substance; and a dispensing system capable of dispensing the neutralizing substance.

In another example, a device for selecting a plurality of precursors to produce an aroma-producing substance includes a container capable of containing each of the plurality of precursors, a selector capable of selecting each of the plurality of precursors, a collecting space for receiving each of the plurality of precursors selected by the selector, a dispensing mechanism for dispensing the aroma-producing substance formed by a plurality of the plurality of precursors.

BRIEF DESCRIPTION OF THE DRAWINGS

The drawings provide specific examples of the invention, but the invention should not be limited merely to the examples disclosed. Instead, the invention should be limited only by the claims that may eventually issue. Many variations in the system, changes in specific components of the system and uses of the system will be readily apparent to those familiar with the art.

FIG. 1 depicts one example of the invention.

FIG. 2 shows another example of the invention.

FIG. 3 depicts a processing module for cyber-assisted olfaction.

FIG. 4 illustrates another example of the invention, as a decontaminator.

FIG. 5 depicts a common pyridinium-imidazolium compound precursor component for forming several antidotes.

FIG. 6 depicts a bis-imidazolium compound precursor component for forming a common antidote that works against soman and tabun.

FIG. 7 depicts examples of the invention used in transportation systems.

FIG. 8 depicts another example of the invention.

FIG. 9 illustrates another example of the invention.

FIG. 10 depicts various derivatives of a bis-pyridinium compound precursor for forming a plurality of antidotes against VX and sarin.

DETAILED DESCRIPTION

The detailed description and drawings provide some examples of the present invention, but the present invention should not be limited merely to the examples disclosed. Instead, the invention should be limited only by the claims that may eventually issue. Many variations in the present invention, changes in specific components of the present invention, and uses of the present invention will be readily apparent to those familiar with the field based on the drawings and descriptions provided. Items of Figures are as Follows:

1. Circular frame
2. Fragrance Capsules
3. Selector (robotic arm)
4. Fragrance alley
5. Exhaust
6. Rectangular frame
7. Cylindrical anti-toxin device
8. Remote Sensor
9. Canister
10. Rotating spindle
11. Hydraulic piston
12. Canister valve
13. Pressurized mixing chamber
14. Diffuser In one example, a device would select a plurality of precursors to produce a neutralizing substance to neutralize a substance. In one example, the substance to be neutralized may be a harmful substance or a lethal substance such as Soman. The term "neutralized" means that the substance to be neutralized may be completely eliminated, or the substance harmful effects is completely reduced or lessened.

The device for neutralizing a substance would include a container that is capable of containing each of the plurality of precursors, a collecting space for receiving each of the plurality of precursors selected by the selector, and a dispensing mechanism for dispensing the neutralizing substance. In one example, the neutralizing substance is formulated by the reactions of the precursors in order to neutralize the substance. The device or the system, as described later, may be termed as a "decontaminator." Alternatively, the term may be a "decontaminator component or neutralizer."

The selector, in one example, may include a mechanical member. In still another example, the mechanical member may include a programmable robotic arm. In addition, the selector may be fitted with a plurality of micro tubes to insure independent transport of chemical precursors or fragrance bases and to avoid unwanted chemical reactions. Selective activation of such tubes will allow for alternate cleansing intervals through interactions between the tubes (to be cleansed) and the decontamination or neutralizing module.

In one example, the container includes a plurality of bubble membranes. Each of the plurality of bubble membranes is capable of containing one of the pluralities of precursors.

In another example, the container is formed by a solid substance and the selector is capable of selecting a controlled amount of at least one of the precursors by liquefying or vaporizing at least a portion of the solid substance.

In still another example, the container is a protective coating selected such that the selector is capable of selecting a controlled amount of at least one of the plurality of the precursors by removing at least a portion of the protective coating.

The device may further include a cleanser component such that undesirable reactions between the precursors or the neutralizing substance are prevented by cleansing the collecting space. Alternatively, the device may be utilized in a fragrance dispenser. The fragrance dispenser would contain a plurality of precursors to produce the aroma producing substance. However, the device would select from the plurality of precursors to produce a neutralizing substance if the aroma-producing substance is harmful or lethal, for example.

In another example, the device selects precursors to make an aroma-producing substance, detecting the substance if it is harmful, and prevents emission of the harmful substance.

In one specific example, a device that is designed to produce aromas is controlled by a computer. The device mixes certain chemicals in order to simulate specific aromas to be generated for enhancing a user's experience when participating in a virtual reality or internet experience. A safety mechanism is provided that detects any production of a hazardous substance which may be caused by combining the chemical compounds used for producing aromas or by malicious intents. Consequently, in one example, if a hazardous substance is detected, then the device prevents the computer from producing the substance using the device. Alternatively, if a hazardous substance is created, then the device produces a neutralizing substance from a plurality of precursors, selects a neutralizing substance, dispenses the neutralizing substance, and neutralizes the hazardous substance.

In a larger scale system, a neutralizing substance may be produced whenever a hazardous substance is detected such as in buildings air handling system. In this case, a detector of bioactive substances may be used to detect any hazardous or irritating bioactive substance. Then, a protective or neutralizing substance may be generated by the system, such as in a filter or a mixing volume, which provides for adequate neutralization of the bioactive substance.

In one example, the neutralizing substance is an oxidizing substance, such as chlorine bleach or other chloride oxidizer, which may be dispensed to neutralize most bioactive substances. However, this solution would be counter indicated if the bioactive substance was a Fahgene gas or other chlorinated gas or acidic substance. In this case, calcium carbonate or baking soda would be able to adsorb and neutralize the bioactive substances. The on-demand system of the present invention would be able to produce the most appropriate neutralizing or preventative substance.

In one embodiment, the device for selecting a plurality of precursors may include a frame for enclosing the device, a container containing the precursors, a selector capable of selecting each of the plurality of precursors, a collecting space for receiving each of the plurality of precursors and a dispensing mechanism for dispensing the aroma-producing substance formed by a plurality of the precursors. In one example, the collecting space is a fragrance "alley" which may receive each of the plurality of substances or aroma-producing substance. Additionally, the collecting space, in one example, is a "fragrance capsule." In one example, the dispensing mechanism includes a discharger for channeling the aroma out of the device through an outlet. In one example, the discharger is a pump-fan combination system. In one example, the outlet may include an exhaust. The device may additionally include a decontaminator component for neutralizing the substance to be neutralized with a neutralizing substance.

Figure 1:
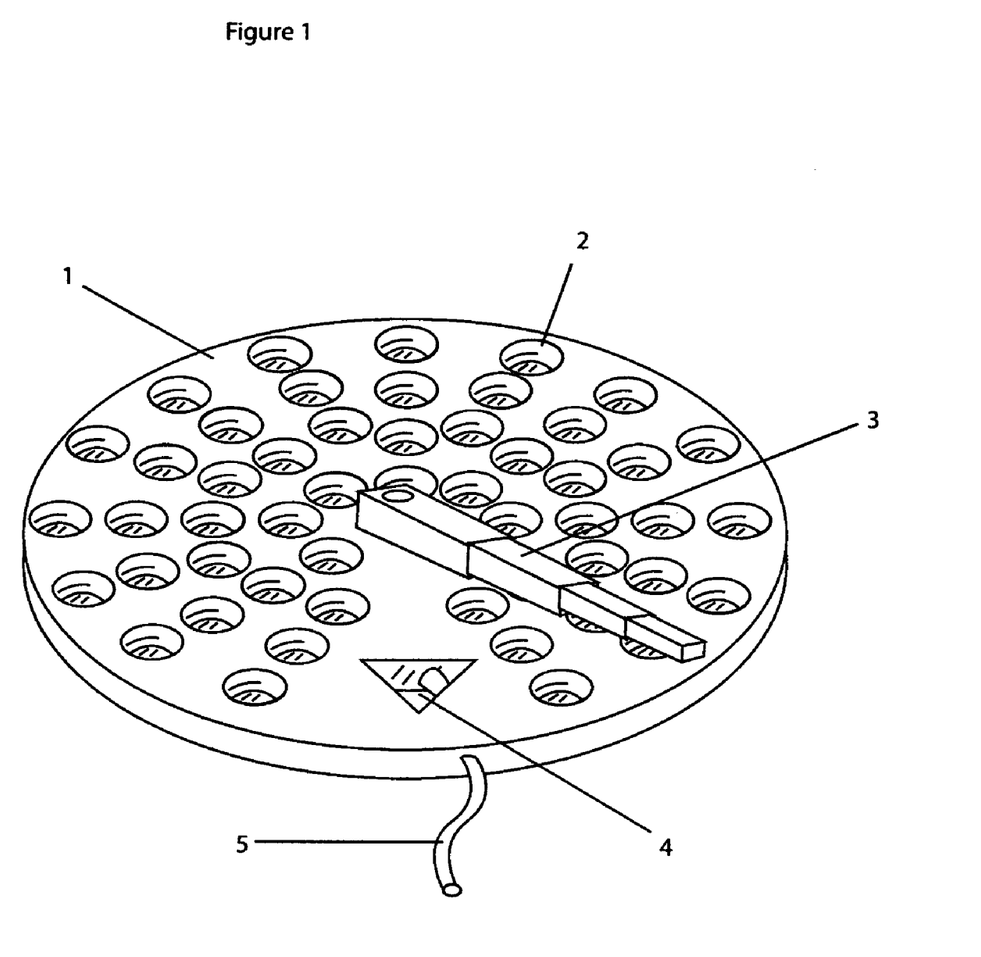

FIG. 1 shows one embodiment that may be designed for the senses of smell and taste. In this embodiment, the device for selecting a plurality of component precursors includes a circular frame for enclosing the device (1), a fragrance capsule (2) containing the precursors, a selector (3) such as a robotic arm for choosing the precursors, a fragrance alley (4) for receipt of the aroma-producing substance, and a discharger such as pump-fan combination system for channeling the aroma out of the device through an outlet such as an exhaust (5). The device may additionally include a decontaminator for neutralizing the harmful substance with a neutralizing substance.

Upon activation of a Graphical User Interface (GUI) script, a controller directs a selector (3) such as a robotic arm to select a fragrance capsule (2). Vapors, mists or particles are released, such as by ultrasonic vibration or ventilation of the opened fragrance capsule (2), which are delivered into the fragrance alley (4) of the apparatus. The fragrance may be activated and boosted inside a reaction chamber which may modify the pressure. In one example, a combination of pumps and fans channels the fragrance through an exhaust (5).

FIG. 1 also illustrates a repository system. As described earlier, a circular frame (1) spinning around its vertical axis, a selector such as a programmable robotic arm (3), fragrance capsules (2) attached to the axis, capsule opener (not shown), fragrance alley (4), compressor/processor chamber, pump-fans combo (not shown), and exhaust (5) are included in the system. Here, the selector (3) may also operate as a capsule opener. In one example, the fragrance capsule (2) contains the precursor components for forming an aroma-producing substance. The fragrance alley (4) receives an aroma-producing substance. In another example, the device may additionally include a fragrance compressor (not shown). The fragrance compressor may further activate the aroma-containing substance before transmission to a pump-fan combination system.

The device may additionally include a cleanser such that undesirable reactions between the precursors or the neutralizing substances are prevented by cleansing the collecting space (4). In one example, the cleanser is a deodorizer. A deodorizer may be used as a cleansing and neutralizing mechanism to cleanse the system of past fragrance compounds. In addition, the deodorizer may be used to prevent dispersion of unwanted or dangerous chemicals that might be accidentally generated by intermixing and chemical reaction of compounds in the system or maliciously created through tempering. In general, information from a sensor (not shown) arrives as data to a central processing unit and a computer (not shown) suppresses or emits a fragrance directly to the user using the device as described in this disclosure.

In one example, a device such as a fragrance scanner (i.e., a biosensor) is envisioned as a means of detecting and encoding natural aromas into digital values. A fragrance dispenser decodes such values and assigns them to a controller which may be digital. In turn, the controller may be capable of directing the selection of compounds by the device of this disclosure to generate a specific fragrance corresponding to the fragrance coding. End users may then make contact with selected fragrance via the exhaust (5) system. For example, while eating an apple, a user may use the apparatus to match the fragrance of the apple to its closest on-board, non-toxic synthetic replica. Moreover, when faced with a new (unregistered) fragrance, the system matches the unregistered information signature of the new element to its closest on-board combination. Optionally, the system may also perform a registry update and allow human operators to choose the closest match from a lookup table, thus, bypassing the function of the biosensor.

Thus, as a growing portion of the population continues to depend on digital gadgets to assist them with daily cyber experiences, there is a need for a system that can process (encode and decode) a particular aroma to facilitate its transmission through digital networks. For example, the device may allow a florist to offer a specimen of his/her products through cyberspace. It may also enable a chef in China to offer tasty samplers of his/her special dish to a customer in the United State of America via the Internet. The device may have implications in E-commerce, Online Advertising, Entertainment, Electronics, Education, and Cyber Terrorism. In one embodiment, a sensor is used to detect fragrances, encodes the fragrances digitally and a fragrance dispenser uses the digital information to recreate the fragrances from an array of heterogeneous chemical precursors available in a chemical storage system.

In one example, as described in the previous examples, the device is a fragrance dispenser. The dispenser may include a fragrance repository (fragrance bank) that contains synthetic aromatic/odorous substances (herein referred to as fragrance bases). Basic precursors of fragrances are used to allow a wide range of fragrances to be created and dispensed. The combination of fragrance bases may produce the aromas most desired for use in cyberspace.

In one embodiment, replaceable cartridges may be provided that contain fragrance bases for specific applications or ranges of aromas to be dispensed.

In one embodiment, the fragrance dispenser dispenses a fragrance by decoding the aromatic value of a product, activating its emission from a computer or computer peripheral device to a user. For example, a graphical representation of a product or object may be detected and an aroma associated with the product or object may be produced. In one example, a look up table approach is used to select the fragrance bases associated with a detected image after it is classified.

Figure 2:
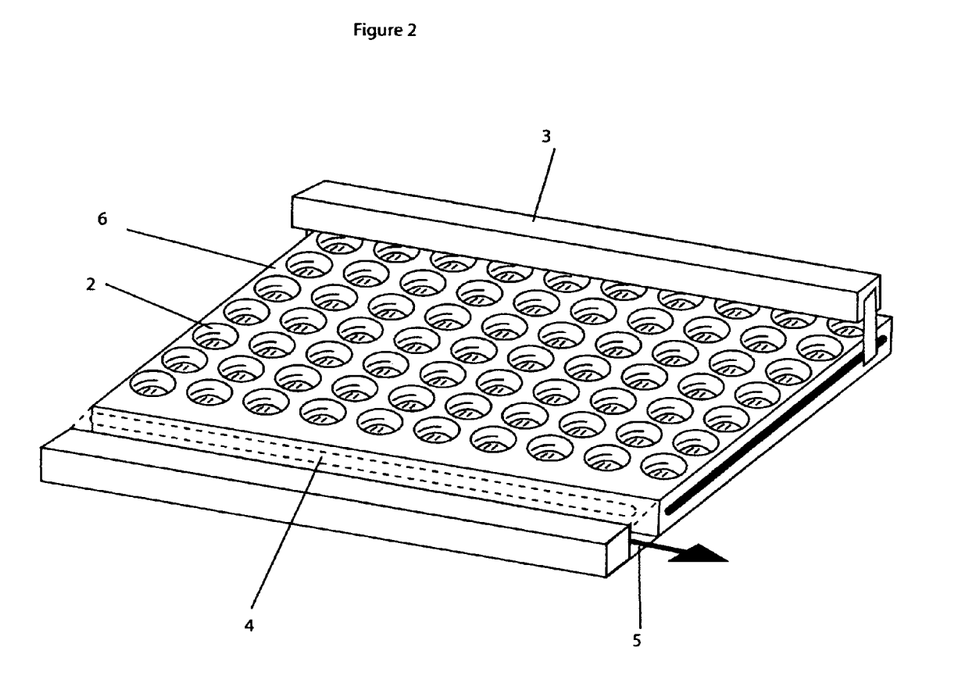

In FIG. 2, another embodiment having a rectangular frame (6), fragrance capsules (2), scrolling fragrance selector (3) such as a scroll bar, a fragrance compressor (4), and an exhaust (5), is illustrated.

In this embodiment, the device for selecting a plurality of precursors to produce an aroma-producing substance includes a rectangular frame (6) for enclosing the device, a fragrance capsule (2) containing the precursors, a selector (3) such as scroll bar with a robotic arm for choosing the precursors, a fragrance alley (4) for receipt of the aroma-producing substance, and a discharger such as pump-fan combination system for channeling the aroma out of the device through an outlet such as an exhaust (5). In this example, the container may be a fragrance capsule (2). In this example, the collecting space may be a fragrance alley (4). The device may additionally include a decontaminator for neutralizing the substance to be neutralized with a neutralizing substance.

In one example, the device may include a fragrance compressor (not shown). The fragrance compressor may further activate the aroma-producing substance before transmission to a pump-fan combination system. Alternatively, the fragrance compressor may allow for further mixing of the precursors of the aroma producing substance.

Aromas may be dispensed in a stand-alone environment. For instance, a computer loaded with one or more fragrance cartridges interacts with programs or multimedia features dispense fragrances. In a stand-alone environment, the cyber-assisted experience is initiated and terminated on the same device. For example, a user may choose to aromatize the experience of an audio CD, a video CD, a DVD, a computer game or a website, such as with the emulation of a rose fragrance from the computer.

Basically the system includes a detecting system capable of detecting and identifying a plurality of substances to be neutralized, an analysis system capable of selecting a neutralizing substance capable of neutralizing the substance to neutralized, a selection system capable of selecting a plurality of precursors to form the neutralizing substance and a dispensing system capable of dispensing the neutralizing system. In one example, the system may be utilized in a fragrance dispensing system.

In one example, the system may include container including a plurality of component precursors to produce an aroma-producing substance, which is coupled to a sensory data register with a controller coupling the register to a central processing unit.

Figure 3:
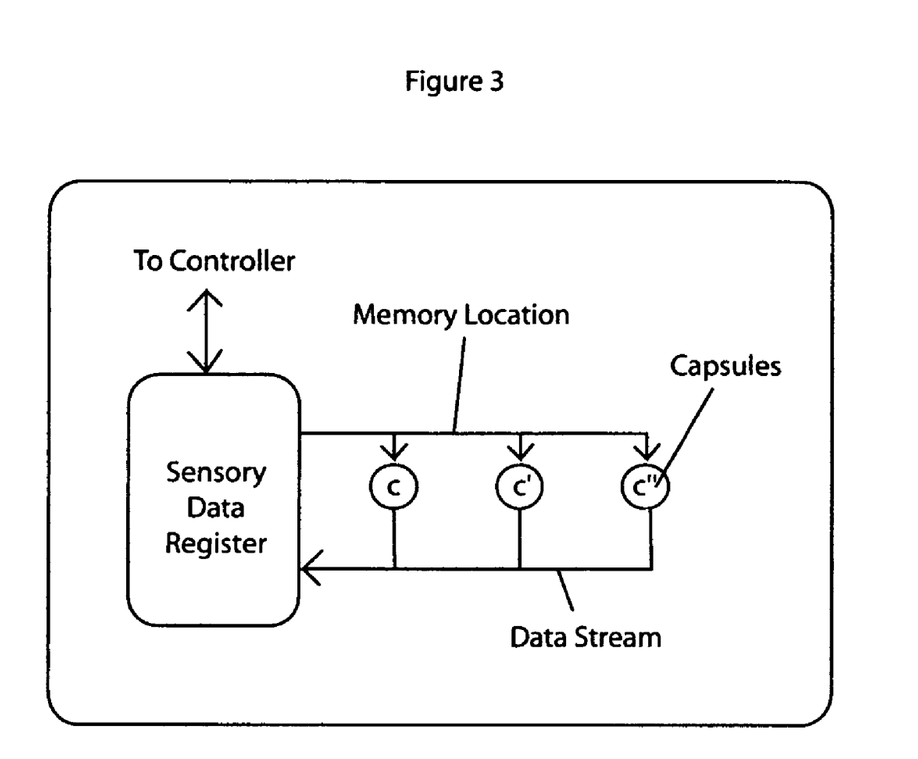

FIG. 3 illustrates a processing module for a cyber-assisted olfaction system. Here, fragrance capsules are shown coupled to a sensory data registry and a controller coupling the register to a central processing unit.

In another embodiment, aromas may be exchanged between computers through a data connection, such as an Universal Serial Buses (USBs) or network connection between two or more computers. The data connection may couple any electronic device. Electronic devices may include a computer, a telecommunication device, a compact disc player and cameras, for example.

A digital fragrance library may be developed to allow the transmission of scripts (such as Visual Basic or JAVA Scripts) that would trigger the dispensing of a fragrance. Digital signal processing (DSP) and digital logic may also be used. For example, a vendor is able to offer a fragrance sampler, such as a cartridge, to a customer which will be used by the customer to smell and/or taste the products of the vendor. This may be vendor specific.

Even printing cartridges currently in-use by computers users around the world might be used to dispense a limited range of taste and smell, if ink is replaced with volatile organic compounds or other substances. For example a perfume sampler may be distributed using an ink-jet printer cartridge with base fragrances inserted in place of the cyan, magenta yellow and black ink.

An ink-jet printer essentially places extremely small heterogeneous droplets of ink onto paper to create a "desirable whole" image. The dots are extremely small (usually between 50 and 60 microns in diameter), so small that they are tinier than the diameter of a human hair (70 microns). The dots are positioned very precisely, with resolutions of up to 1440×720 dots per inch (dpi). The dots can have different colors combined together to create photo-quality images. Through a similar process, for example, the proposed apparatus may produce an on-demand chemical compound (fragrance or antidote).

In order to prevent tampering with these cartridges, which could be used to insert a hazardous substance or irritant, an ultra thin digital strip may be used. Once broken or tampered with, the strip is programmed to completely disable the cartridge's dispensing abilities. The strip could be used for ink cartridges, microprocessors, or any digital circuit.

Another measure for protecting the user from an accidental or intentional assault on the senses may be to identify a substance in transit to a user, perform a security diagnostic test, and allow or block an unwanted substance. The measure may block the creation of the substance from a dispenser or may filter or neutralize a substance once generated prior to reaching the user. In one example, a neutralizing substance neutralizes a detected, unwanted substance.

In another example, a computer program is capable of warning a user of a threat. The fragrance dispenser may be supplied with fragrance bases, such as gamma-Valeroactone ($C_5H_8O_2$), gamma-Heptalactone ($C_7H_{12}O_2$) and Rosa damascena/rose oxide ($C_{10}H_{18}O$), and may also contain chemical neutralizers or antidotes such as atropine ($C_{17}H_{23}NO_3$), chlorine dioxide ($ClO_2$), or pure sodium bicarbonate ($NaHCO_3$) to counter hazardous substances and other undesirable chemicals. Isotopic fractionation may be used to facilitate olfaction. If an undesirable substance is detected, along with blocking the undesirable substance, the advisory system will alert the user for further investigation.

In one example, the system offers a quarantine-before-inhalation approach to biochemical warfare, as opposed to the traditional rescue-after-contamination practice of removing a victim from the affected area before applying treatments. Ideally, according to this new model (quarantine-before-inhalation), the unwanted substance is adsorbed or neutralized prior to reaching the user.

Figure 4:
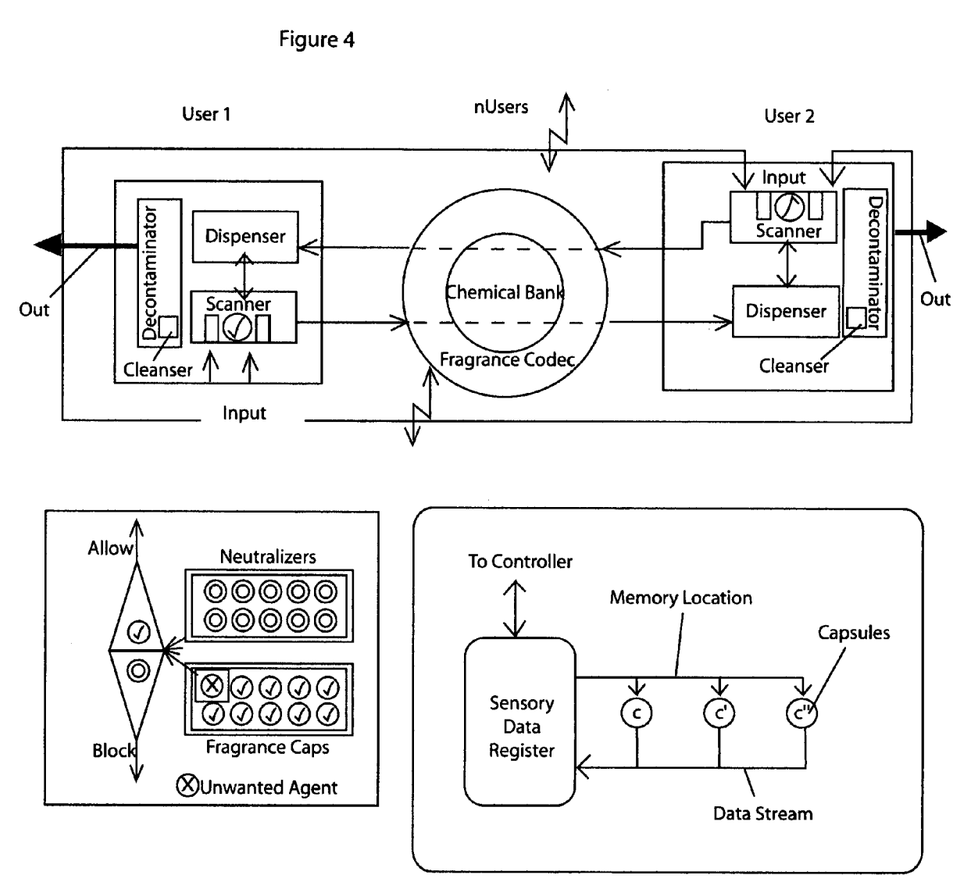

FIG. 4 illustrates one example of a decontaminator system. The top section illustrates interactions between users engaged in the exchange of smell and/or taste through a network. Users scan (scanner) a fragrance or select a particular code (Fragrance Codec) trigger the dissemination (dispenser) of aromatic/gustative particles through an (exhaust). The cleanser and the decontaminator are also displayed. The bottom left section describes the decontamination process. The last section illustrates the data processing module.

The decontaminator, in one example, selects a plurality of precursors to form a neutralizing substance.

In one example, the cleanser may be coupled to the decontaminator and prevent unwanted inadvertent reactions of the precursors. In one example, the cleanser is a deodorizer for preventing dispersion of unwanted reactions.

Neurotransmitters, the key information molecules of the brain, mediate the actions chemicals and drugs in the central nervous system (CNS). These molecules account for diverse chemical classes, including the biogenic amines, amino acids, peptides, and gases. For instance, acetylcholine (ACh), potent excitatory neurotransmitter acting at muscarinic and nicotinic receptors, plays a major role in the activities of the CNS.

Organophosphorus (OP) compounds, as described in the *Journal of MedicalChemical Defense*, are potent poisons that phosphylate the catalytic site of acetycholinesterase (ACHE) and inhibit the enzyme[1]. Oximes, for example, are antidotes against OP poisoning because they reactivate the inhibited enzyme due to their nucleophilic properties and high affinity for the enzyme.

[1] Primozie et al. (2004). Pyridinium, Imidazolium, and Quinuclidinium Oximes: Synthesis, interaction with native and phosphylated cholinesterases, and antidotes against organophosphorus compounds. *Journal of Medical Chemical Defense*, vol., 2, 6: 1-30.

Oximes, for example, reactivate phosphylated cholinesterases by displacing the phosphoryl moiety from the enzyme. Enzymatic activity is restored and the de-phosphylated enzyme and phosphylated oximes are formed.

It is well known that oximes are considered the most effective antidotes to combat OP poisoning, for they reactivate the inhibited enzyme due to their nucleophilic properties. The treatment of poisonings produced by AChE inhibitors has remained practically unchanged for many decades with the synergetic success of muscarinic antagonist atropine and the most effective oximes available.

According to their molecular structures, AChE-blocking substances may be classified into at least two groups: organophosphates (OPs) and carbamates (See, Heyl, W. C. Harrs, L. W., and Stitcher, D. L. (1980). Effects of carbamates on whole blood cholinesterase activity: chemical protection against soman. *Drug Chem. Toxicol.* 3, 319-332; Marrs, T. C. (2000). Toxicology of pesticides. In General and Applied Toxicology (B. Ballantyne, T. C. Marrs, and T. Syversen, Eds.), pp. 1993-2012. Macmillan, London).

Among AChE inhibitors, particular attention has been given OP nerve gases such as sarin (GB), soman (GD), tabun (GA), and cyclo-sarin (GF) as chemical warfare substances.[2]

[2] See Gordon, J., Leadbeater, L., and Maidment, M. (1978). The protection of animals against organophosphate poisoning by pretreatment with a carbamate. *Toxicol. Appl. Pharmacol*, 207-216; Holstege, C., Kirk, M., and Sidell, F. (1997). Chemical warfare. Nerve substance poisoning. *Crit. Care Clin.*, 923-942; and Ohbu, S., Yamashina, A., Takasu, N. Yamaguchi, T., Murai, T., Nakano, K., Matsui, Y., Mikani, R., Sakurai, K., Hinohara, S. (1997). Sarin poisoning on Tokyo subway. *South. Med. J.*, 587-593.

There are at present at least four widely known nucleophilic substances, which have proven very effective both as reactivators of the phosphylated ACHE, and as antidotes in OP poisoning: (1) PAM- and HI-(monooxime) and (2) Toxogonin and TMB-(dioximes). Other derivatives of these nucleophilic substances have also been proposed.

In one embodiment of the invention, at least one of the plurality of precursors is a common precursor for forming a plurality of neutralizing substances for neutralizing a plurality of different substances to be neutralized. In one example, the decontaminator selects common precursors to form at least two different neutralizing substances for at least two different chemical threats. An antidote is one example of a neutralizing substance.

In many of the neutralizing substances proposed, the antidote bases will derive from a combination of oximes.

Primozic et al. (2004) tested oximes for their reactivating potency using native human erythrocyte Acetycholinesterase (ACHE) inhibited by Sarin, Soman, Tabun or VX. The reactivating potency of the oximes was determined by incubating washed erythrocytes with the organophosphate for 15 minutes at 4 degrees Celsius. Reactivation was started by dilution of the reaction mixture with the oxime solution at 37 degrees Celsius. Oxime concentration was 0.020 mM and after 30 minutes, the activity of the reactivated enzyme was measured, and the result expressed as percent reactivation. The accompanying FIGS. 5 and 6 describe the group results and may be applicable to an embodiment of the invention.

In the experiments conducted by Primozie et al. (2004), the majority of prepared compounds were pyridinium oximes: In vitro studies comprised reversible inhibition of cholinesterases, protection of cholinesterases from phosphylation by organophosphorus compounds (OP), and reactivation of the phosphylated enzyme. In vivo studies of the oximes as antidotes in experimental poisoning by OP compounds are also reviewed.

In one example, as shown in the accompanying FIG. 5 a common precursor compound, herein abbreviated as PyIm, forms several antidotes for two different lethal substances, Soman and Tabun.

In another example, PyIm forms PyIm-5 (Mesić et al., 1991),[3] with the addition of two benzyl groups to the "a" portion of the molecule PyIm-5 to reactivate a tabun-phosphorylated enzyme by 20%. In another example, PyIm with the addition of 4 phenyl groups to the "a" portion of the molecule form PyIm-8 which also reactivates a tabun-phosphorylated enzyme by 20%.

[3]Mesić, M., Deljac, A., Deljac, V., and Binenfeld, Z. (1991). Reactivators of acetylcholinesterase inhibited by organophosphorus compounds. Imidazole derivatives. II. *Acta Pharm Jugosl.* 41, 203-210.

Yet, in another example, PyIm with the addition of 4 p-methoxybenzen groups to the "a" portion of the molecule forms PyIm-10 which also reactivates a Tabun-phosphorylated enzyme by 20%.

The same precursor, PyIm, with the addition of 2 ρ-methylbenzen groups to the "a" portion of the molecule, forms PyIm-13 (Mesić et al., 1994),[4] which reactivates a Soman-phosphorylated enzyme by 35%. Thus, as shown in these examples, the proposed autonomous decontamination system can selectively choose a common precursor (e.g., PyIm) for two neutralizing substances (such as PyIm-5 and PyIm-13) for two different lethal substances (such as Tabun and Soman respectively).

[4]Mesić, M, Roncević, R., Radić, B., Fajdetić, A., and Binenfeld, Z. (1994). Reactivators of acetylcholinesterase inhibited by organophosphorus compounds. Imidazole derivatives. V. *Acta Pharm.* 44, 145-150.

In another embodiment of the invention, according to FIG. 6, a common precursor, herein described as a bis-imidazolium compound (Im2). Im2, with the addition of a phenyl group to the "R" portion of the molecule, a ($CH_2$) group to the "Y" portion, and 2 Bromine of "X", forms Im2-13 (Deljac et al., 1992).[5] Im2-13 may serve as a common antidote for both Soman and Tabun (although the reactivation effect on an enzyme such as ACHE may be significantly different). In one example, Im2-13 reactivates a Tabun-inactivated enzyme by 20% (Deljac et al., 1992; Mesić et al., 1991). In another example, (the same) Im2-13 reactivates a Soman-inactivated enzyme by 71% (Radić et al., 1999).[6] Therefore, as shown in these examples, decontaminator may selectively produce a common precursor (e.g., Im2) that will form one antidote (Im2-13) that is more effective for one lethal substance (71% for soman) than another lethal substance (20% for Tabun).

[5]Deljac, V., Deljac, A., Mesić, M., Kilibarda, V., Maksimovic, M., and Binenfeld, Z. (1992) Reactivators of AChE inhibited by organophosphorus compounds. Butenylenic and tetramethylenic heterocyclic oximes. IV. *Acta Pharm.* 42, 173-179.
[6]Radić, B., Lucić, A., Peraica, M., and Bradamante, V. (1999) Treatment of carbamate and organophosphate intoxication with new oximes. *Acta Pharm.* 49, 71-77.

Figure 10:
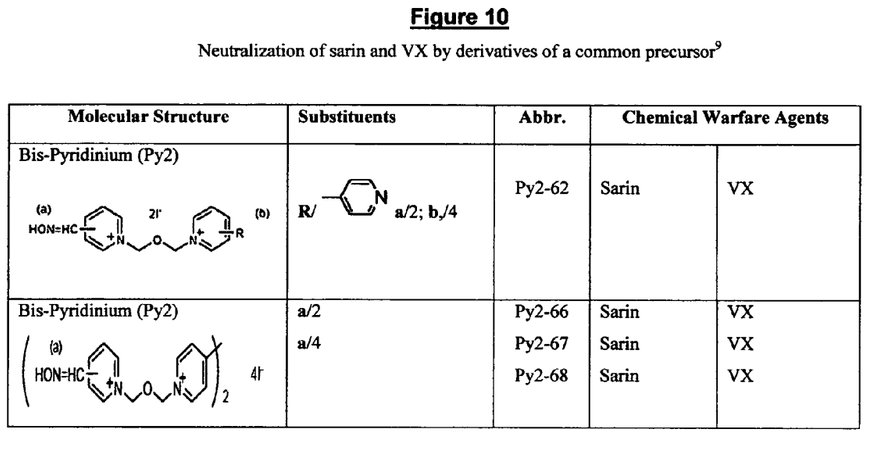

As illustrated in FIG. 10, further manipulations of the molecular structure of bis-pyridinium (Py2) also yield to (Py2-62, Py2-66, Py2-67, and Py2-68). These oximes are good reactivators of ACHE and have a high therapeutic factor (TF) against VX and sarin (Bregovec et al., 1984[7]; Aas, 2003; Primmozic et al., 2004).

[7]Bregovec, I., Binenfeld, Z., Maksimović, M., and Bošković, B. (1984). Synthesis and therapeutic effects of bipyridyl pyridine aldoxime derivatives in poisoning by anticholinesterase agents. *Acta Pharm Jugosl.* 34, 133-138.

Based on the foregoing results, it is evident that an autonomous biochemical decontamination system may selectively choose a given precursor to form an antidote that is (a) more effective for one lethal substance over another, (b) able to neutralize more than one lethal substance, and (c) a derivative of a plurality of precursors.

Figure 7:
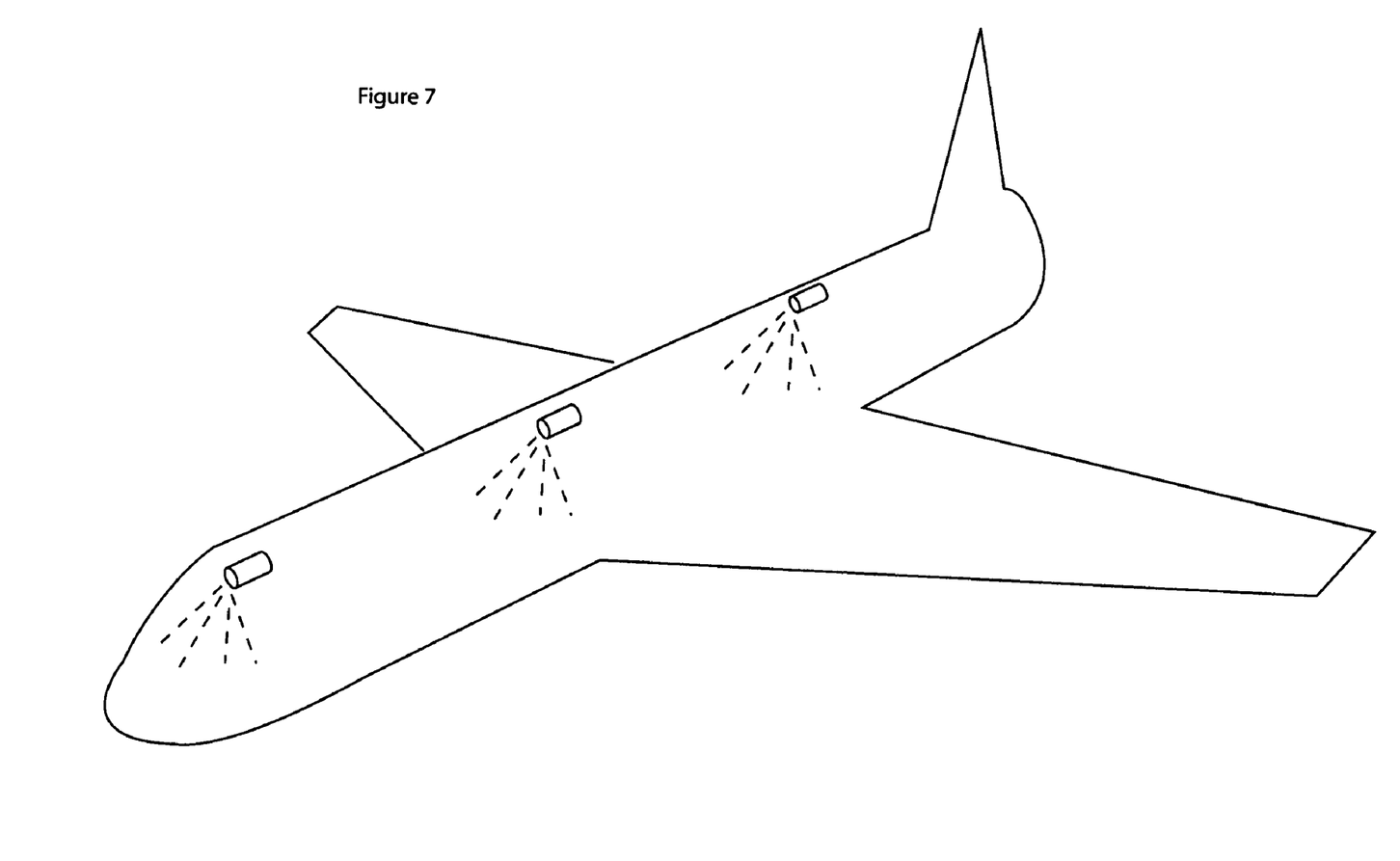

In one embodiment, the decontaminator may be embedded in tunnels, subways stations, and inside train cars to initiate automatic decontamination of affected areas. It may be installed in airport facilities and other channels of mass transits. Moreover, the decontaminator can also be installed in the ventilation system of buildings, such as churches, schools, hospitals and arenas. As shown in FIG. 7, the decontaminator is shown utilized in an airplane, but could also be used in places such as a church, a cruise ship, or a subway.

In another embodiment, the decontaminator system may include a sensor for distinguishing between two types of lethal substances. Gordon et al (2002), in U.S. Pat. No. 6,406,876, describes a differential biosensor which may be made of cholinesterases, hydrolases of organophosphorous and organosulfur and laccase which each is individually and separately secured onto a carrier such as piece of plastic. In this example, OP refers to both organophosphorus and organosulfur. For example, serum OP hydrolase from rabbit exhibits high activity with sarin but not with soman. In another example, Gordon describes higher enzymatic activity of OP hydrolase against soman than for sarin or for tabun. However, Gordon did not disclose system and apparatus that would aerosolize a "confined space" for the purpose of neutralizing said space.

Although Wood, et al. (1982) in U.S. Pat. No. 4,342,834 discloses a method of making isocyanate-based polyurethane foams wherein enzymes having varying degrees of activity are covalently linked, it does not disclose a method of using this method to detect and neutralize airborne bioactive substances such as soman and tabun in a confined space.

Yoshida, et al. (1980) in U.S. Pat. No. 4,226,938 discloses a method for immobilizing enzymes thereby said enzymes are adsorbed on an adsorbent powder in an aqueous medium and a water-miscible monomer is added thereto, and said monomer is polymerized to form a porous gel lump through which a substrate solution can freely pass. However, Yoshida et al. (1980) did not address the issue of aerial neutralization of bioactive substance in confined spaces, nor did they propose a system-of-systems that autonomously detects, identify, warn, and neutralize bioactive substances (e.g., chemical warfare agents).

In one example, the decontaminator detects the presence of neurotoxic substances. Such neurotoxic substances include organophosphorus substances that are potent poisons that phosphylate the catalytic site of acetylcholinesterase, an enzyme that catalyzes the breakdown of acetylcholine. Such organophosphate compounds include sarin, soman, tabun, and cyclo-sarin.

Figure 8:
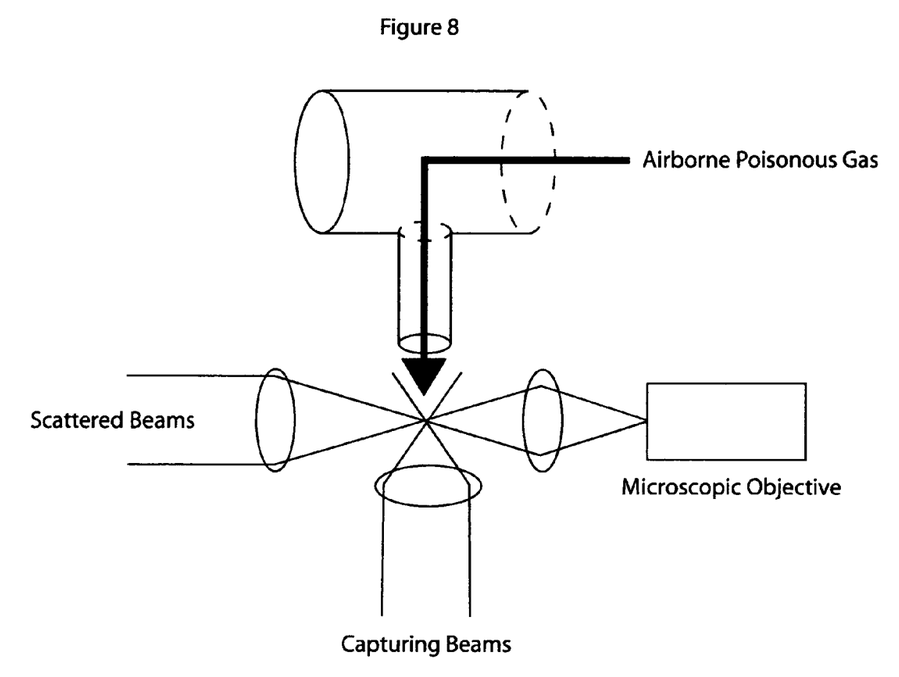

In another embodiment as shown in FIG. 8, an assembly of chemical sensors (which may be of various types) identify biochemical substances according to their molecular structures, for examples, and produce a neutralizing substance in situ. A direct identification by calibration against known hazards may be used or detection by molecular structure may be used to allow scanning of an extended array of chemical substances. Moreover, sequence-based identification using nucleic acid assays (and similar techniques such as function-based and cell-based detection systems) can play an important role in the detection and analysis biological warfare agents.[8] In this way, even an unknown hazardous substance may be identified and consequently partially neutralized. For example, DNA pattern-recognition techniques may be used to detect hazardous biological substances and match such substances against on-board neutralizing substances.

[8] Nelson, K., Paulsen, J., Heidelberg, and Fraser, C. (2000). Status of genome projects for nonpathogenic bacteria and archea. Nature Biology 18, 1049-1054; Radnedge, L., Gamez-Chin, S., McCready, P., Worsham, P., and Andersen, G. (2001). Identification of nucleotide sequences for the specific and rapid detection of *Yersinia pestis*. Appl. And Env. Microbio. 67, 3759-3762.

A hand-held embodiment of this device may consist of a compact antidote tank (e.g., a cylinder) surmounted by multi-array biochemical sensors. The detection component may comprise a plurality of multi-array sensors of various types. A sensory data fusion (SDF) module may synchronize the complex heterogeneous data mining and processing procedures from these sensors through a neural network. In the presence of a bioactive substance, human operators will be alerted to activate the device by releasing antidote fluid in the air to provoke an aerosol-based environmental decontamination reaction. This unit can be mass-produced at a more reasonable cost than the autonomous system, which is intended to work in much larger structures.

Other potent ACHE inhibitors include carbamates. Both organophosphorus substances and carbamates are widely employed as insecticides as well. In a still further example, the biochemical decontaminator detects the neurotoxic substance and renders the neurotoxic substance by selecting a minimum amount of neurotoxic antidote to render the neurotoxic substance less toxic and need not completely neutralize the neurotoxic substance. In one example, the biochemical decontaminator utilizes an oxime to neutralize an organophorus substance. In still other examples, the decontaminator may select a neurotoxic antidote from (1) PAM-2 and HI-6 (monooxime), (2) Toxogonin and TMB-4 (dioximes), or (3) or a combination of such neurotoxic antidotes.

In still other examples, the decontaminator utilizes an aerosol form of a neurotoxic antidote. However, the aerosol formula from such neurotoxic antidote or combination of such neurotoxic antidotes is not limited the antidotes discussed herein.

It is important to note that the volume of the antidotes dispersed varies with the type of substance and the concentration of the substance, which can be measured by chemical means such as chromatographic or mass spectrometric instruments. For example, the concentration of atropine is different in nerve substance intoxication from that of insecticide poisoning. Furthermore, the volume of aerosol needed to decontaminate a jumbo jet may be different from the volume needed for a computer casing.

Figure 9:
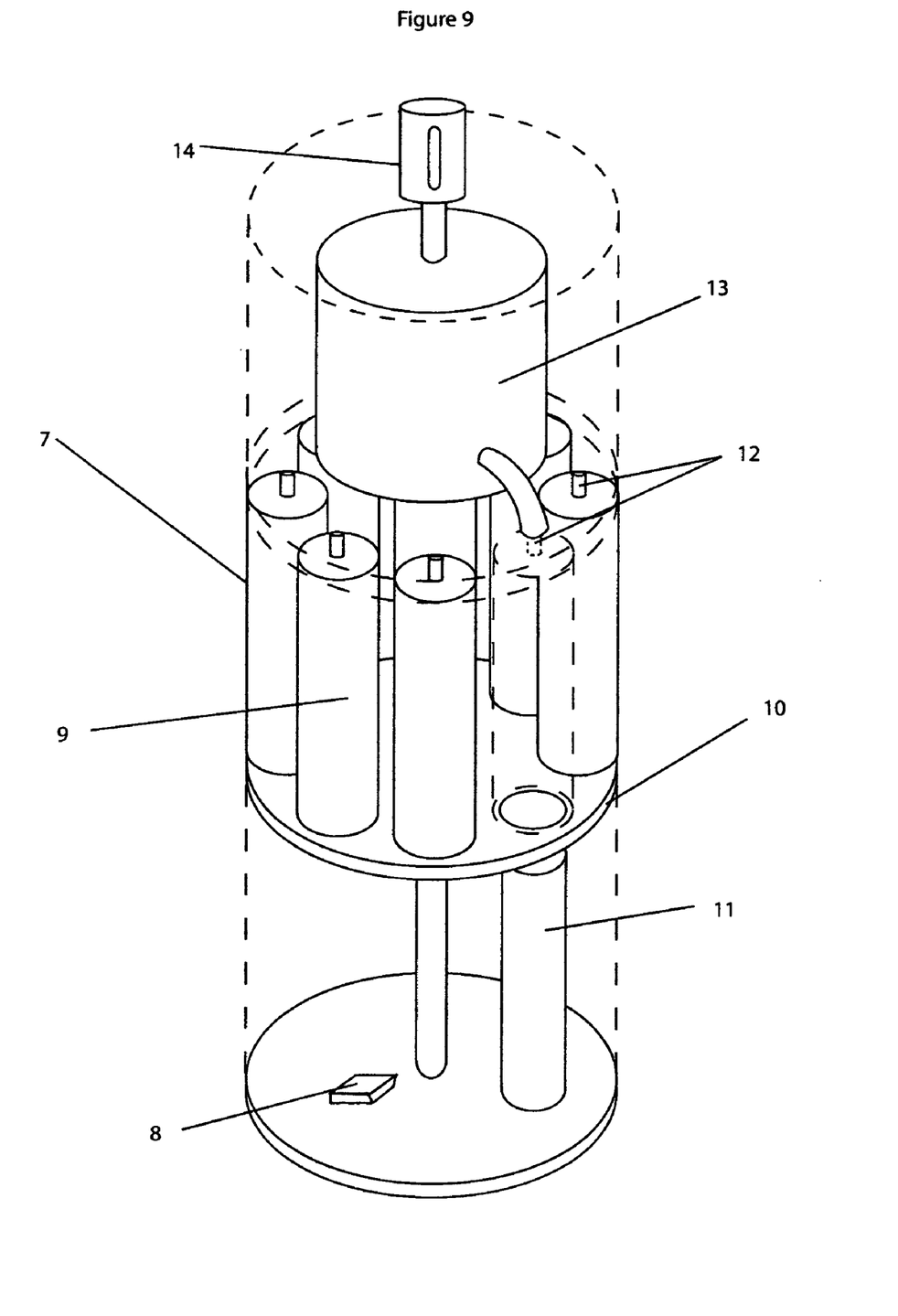

As shown in FIG. 9, another embodiment of the device may consist of a portable unit that operates more like a "cylindrical fire extinguisher" to work in small and medium size structures (for example, in churches, restaurants, and private homes). Upon detection of a specific bioactive substance by a third party sensor, the portable unit could then be activated to neutralize a bioactive substance and minimize its intended (malicious) effect. One way of operating such a cylindrical anti-toxin device (7) would be as such. A signal could be received via a remote sensor (8), which would notify the device of a particular hazard. The device could then release a variable amount of anti-toxins from a given canister (9) on a rotating spindle (10). A hydraulic piston (11) is shown as the means of pumping out a given amount of anti-toxic material. As per the information received by the remote sensor (8), different amounts of anti-toxins can be released from each individual canister (9) as needed. The hydraulic piston (11) would push said anti-toxin through a canister valve (12) into a pressurized mixing chamber (13). When the components necessary to combat the toxin received from the original air analysis are present in the mixing chamber (13), the final mixture is released through a diffuser (14), bringing equilibrium to the given air space.

In the automotive industry, an embodiment of this device may detect smoke (due to excessive heat or flames) and automatically activate the flow of anti-smoke and fire extinguishing fluid. When carefully retrofitted into existing motor vehicles, the device may provide fast response to fire and smoke that tend to make the scene of an accident not visible or aggravate traffic accidents or engine malfunctions. It is important to note that this embodiment may be used both in cars and ships to help put-down minor fire and smoke or widen the window of opportunity to rescue personnel.

The antidote formula may be stored as a vapor, powder, or liquid. A hybrid storage system is also conceivable to overcome the half-life syndrome and address the cost issues associated with replenishment of antidote cartridges. The half-life expectancy of most chemicals depends on storage conditions (chemical state and containers properties). This hybrid concept is built on the principles of binary chemical weapons. Based on that theory, chemicals are not "weaponized" until they are ready for deployment. The binary principle tremendously increases shelf-life and exponentially decreases the risk associated with storage. Similarly, the antidote formula may be subject to final chemical reaction right before dispersion.

Another embodiment may be used in monitoring water supplies against bioterrorism by automatically detecting, warning, and cutting-off water flow until further laboratory probes determine the extent of the contamination. As water sprinkler systems allow or suspend water flow through a pipe, a cost-effective embodiment of this apparatus can do the same for an entire community, in the event of a bio-chemical attack on the water supply. The device may also be placed as a biohazard "stopper" at the terminus of tap water lines.

In another embodiment, the decontaminator may be uploaded with various antidotes and may administer medicine from a remote location. In such a manner, the decontaminator may function as a robotic pharmacist executing remote (digital) prescriptions. For instance, stranded individuals/animals at a dangerous location can be cared for through remote medicine administration. There again, it is safer to take a binary approach insure the proper dosage is delivered at the right time to the right person and in the safest manner.

In agronomy and botany, plants in unreachable areas and animals in unsafe location can receive therapeutic assistance.

Future effort may involve remote/mobile peripheral devices (with the ability to scan, beam, slide, roll, or fly) that will facilitate the tasks of locating and mapping the trajectory of an aerosol or measuring and recording "near-perfect" positions of an airborne chemical's point of release.

The device may encourage pharmaceutical companies to further develop drugs that can be administered through inhalation, for the popularity of cyber-assisted olfaction will facilitate drug distribution through new channels and different locations. For example, a group of individuals in need of medicine might not be accessible to medical staff. Consequently, with the use of this apparatus, medicine may be administered through cyber-assisted medicine (e.g., machine-assisted injection and/or cyber-assisted olfaction).

Alternative combinations and variations of the examples provided will become apparent based on this disclosure. It is not possible to provide specific examples for all of the many possible combinations and variations of the embodiments described, but such combinations and variations may be claims that eventually issue.

What is claimed is:

1. A device for selecting a plurality of precursors to produce a neutralizing substance for a substance to be neutralized, comprising a container capable of containing each of the plurality of precursors, a selector capable of selecting each of the plurality of precursors, a collecting space for receiving each of the plurality of precursors selected by the selector, and a dispensing mechanism for dispensing the neutralizing substance formed by a plurality of the plurality of precursors wherein the container is formed by a solid substance, and the selector is capable of selecting a controlled amount of at least one of the plurality of precursors by liquefying or vaporizing at least a portion of the solid substance such that the neutralizing substance is formulated to neutralize the substance to be neutralized.

2. The device of claim 1, wherein the selector includes a mechanical member.

3. The device of claim 2, wherein the mechanical member includes a programmable robotic arm.

4. The device of claim 1, wherein the container includes a plurality of bubble membranes, each of the plurality of bubble membranes being capable of containing one of the pluralities of precursors.

5. The device of claim 1, wherein the container has a protective coating selected such that the selector is capable of selecting a controlled amount of at least one of the plurality of precursors by removing at least a portion of the protective coating.

6. The device of claim 1, further comprising a cleanser such that undesirable reactions between the precursors or the neutralizing substances are prevented by cleansing the collecting space.

7. A device of claim 1, wherein the device is utilized in a fragrance dispenser such that the neutralizing substance is produced for the substance to be neutralized is an aroma-producing substance.

8. The device of claim 1, wherein the container comprises replaceable cartridges.

9. The device of claim 1, wherein a combination of a plurality of the plurality of the plurality of precursors forms the neutralizing substance such that the neutralizing substance acts as an antidote.

10. The device of claim 1, wherein a combination of a plurality of the plurality of precursors forms the neutralizing substance such that the neutralizing substance is an oxidizing substance.

11. The device of claim 10, wherein one of the plurality of precursors, is sodium hypochlorite.

12. The device of claim 10, wherein one of the plurality of precursors, is calcium oxide and another one of the plurality of precursors, is calcium dioxide, such that calcium carbonate is formed.

13. The device of claim 10, wherein one of the plurality of precursors, is sodium carbonate and another one of the plurality of precursors, is carbon dioxide, such that sodium bicarbonate is formed.

14. The device of claim 1, wherein at least one of the plurality of the precursors is a common precursor for forming a plurality of neutralizing substances for neutralizing a plurality of different substances to be neutralized.

15. The device of claim 14, wherein one of the pluralities of the precursors is Pylm, such that, in combination with other of the plurality of precursors, the neutralizing substance formed is a substance selected from the group of neutralizing substances consisting of Pylm-5 and Pylm-13.

16. The device of claim 1, wherein a combination of a plurality of the plurality of the plurality of precursors forms the neutralizing substance such that the neutralizing substance acts as a medicine.

17. The device of claim 1, wherein a combination of a plurality of the plurality of the plurality of precursors forms the neutralizing substance such that the neutralizing substance acts as a reversible sedative.

18. A device for selecting a plurality of precursors to produce a neutralizing substance for a substance to be neutralized, comprising a container capable of containing each of the plurality of precursors, a selector capable of selecting each of the plurality of precursors, a collecting space for receiving each of the plurality of precursors selected by the selector, and a dispensing mechanism for dispensing the neutralizing substance formed by a plurality of the plurality of precursors such that the neutralizing substance is formulated to neutralize the substance to be neutralized further comprising a sensor for detecting soman and a substance to be neutralized selected from the group of substances consisting of sarin and tabun.

19. The device of claim 18, wherein the sensor is capable of detecting and distinguishing soman from sarin or tabun.

20. The device of claim 19, wherein the sensor exhibits a serum organophosphorous hydrolase activity with sarin but not soman.

21. The device of claim 19, wherein the sensor exhibits a organophosphorous activity that is higher for soman than for tabun.

22. A device for selecting a plurality of precursors to produce an aroma-producing substance comprising a container capable of containing each of the plurality of precursors, a selector capable of selecting each of the plurality of precursors, a collecting space for receiving each of the plurality of precursors selected by the selector, and a dispensing mechanism for dispensing the aroma-producing substance formed by a plurality of the plurality of precursors wherein the container is formed by a solid substance, and the selector is capable of selecting a controlled amount of at least one of the plurality of precursors by liquefying or vaporizing at least a portion of the solid substance.

23. The device of claim 22, further comprising a frame to support all elements of said device wherein said frame may be spherical or rectangular.

24. The device of claim 22, further comprising a microprocessor that controls the selector, receiving order and condition of said plurality of precursors in the collecting space, and dispensing mechanism, such that a final desirable antidote or aromatic compound is created.

25. The device of claim 22, further comprising a compressor for further activation of the plurality of precursors.

26. The device of claim 22, wherein the container is a fragrance capsule, the selector is a robotic arm with a spiraling axle, and the dispensing mechanism includes a discharger for channeling the aroma-producing substance through an outlet.

27. The device of claim 26, wherein the discharger includes a pump-fan combination system and an exhaust.

28. The device of claim 26, further comprising a spherical frame.

29. The device of claim 22, wherein the container is a fragrance capsule, the selector is a scroll bar with the robotic arm, and the dispensing mechanism includes a discharger for channeling the aroma-producing substance through an outlet.

30. The device of claim 29, wherein the discharger includes a pump-fan combination system and an exhaust.

31. The device of claim 29, further comprising a rectangular frame.

32. The device of claim 22, wherein one of the plurality of precursors is rose oxide.

33. The device of claim 22, wherein one of the pluralities of precursors is gamma-Hepatalactone.

34. The device of claim 22, further comprising a data connection capable of coupling an electronic device.

35. The device of claim 34, wherein the electronic device is selected from the group of electronic devices consisting of a computer, a telecommunication device, compact disc players, and cameras.

36. The device of claim 34, wherein the electronic device is a telecommunication device.

37. The device of claim 36, wherein the telecommunication device is a cellular phone or a personal digital assistant.

38. The device of claim 22, further comprising a cleanser such that undesirable reactions between the precursors or the neutralizing substances are prevented by cleansing the collecting space and other related peripheral accessories.

39. The device of claim 38, wherein the cleanser is a deodorizer for preventing dispersion of the unwanted reactions.

* * * * *